(12) United States Patent
Black et al.

(10) Patent No.: US 9,597,095 B2
(45) Date of Patent: Mar. 21, 2017

(54) SCREW GUIDE AND TISSUE RETRACTOR INSTRUMENT

(75) Inventors: Michael Black, Swarthmore, PA (US); Gary Dix, Crownsville, MD (US); Carl Lauryssen, Beverly Hills, CA (US)

(73) Assignee: GLOBUS MEDICAL, INC, Audubon, PA (US)

(*) Notice: Subject to any disclaimer, the term of this patent is extended or adjusted under 35 U.S.C. 154(b) by 914 days.

(21) Appl. No.: 12/781,583

(22) Filed: May 17, 2010

(65) Prior Publication Data

US 2010/0298647 A1   Nov. 25, 2010

Related U.S. Application Data

(60) Provisional application No. 61/178,710, filed on May 15, 2009.

(51) Int. Cl.
| | |
|---|---|
| *A61B 1/32* | (2006.01) |
| *A61B 17/17* | (2006.01) |
| *A61B 17/02* | (2006.01) |
| *A61B 17/00* | (2006.01) |

(52) U.S. Cl.
CPC ...... *A61B 17/1757* (2013.01); *A61B 17/0218* (2013.01); *A61B 17/1703* (2013.01); *A61B 2017/0046* (2013.01)

(58) Field of Classification Search
CPC ....... A61B 1/313; A61B 1/3135; A61B 1/317; A61B 17/7085; A61B 17/7083; A61B 17/0218; A61B 17/0206; A61B 1/32; A61B 17/708; A61B 17/7077

USPC ....... 600/193, 196, 197, 213, 214, 215, 216, 600/219, 226, 227, 228, 229, 230, 234, 600/238

See application file for complete search history.

(56) References Cited

U.S. PATENT DOCUMENTS

| | | | | |
|---|---|---|---|---|
| 1,615,169 | A * | 1/1927 | Ellis | B25B 13/08 81/177.8 |
| 4,934,352 | A * | 6/1990 | Sullivan, Jr. | A61B 17/02 600/213 |
| 5,755,721 | A * | 5/1998 | Hearn | A61B 17/1728 606/104 |
| 6,167,787 | B1 * | 1/2001 | Jarvis | B25B 23/0021 81/177.2 |
| 6,520,053 | B2 * | 2/2003 | Liao | B25G 1/085 81/177.4 |
| 6,572,540 | B2 * | 6/2003 | Dobrovolny | A61B 17/02 600/226 |
| 6,610,080 | B2 * | 8/2003 | Morgan | A61B 17/0401 606/218 |
| 6,929,606 | B2 * | 8/2005 | Ritland | A61B 17/1757 600/201 |

(Continued)

*Primary Examiner* — Lynnsy Summitt (57) ABSTRACT

An apparatus is provided for performing spinal surgery having a handle assembly, a screw guide, and a retractor. A shaft is provided with a handle, a neck portion and a connecting portion. The screw guide is provided with a connecting element coupled to the connecting portion of the handle assembly. A retractor for retracting tissue is coupled to the screw guide, wherein the neck portion of the handle assembly is provided with a spring loaded sleeve adapted to engage one of a plurality of holes positioned on a portion of the connecting element. The connecting portion is pivotably coupled to the connecting element.

20 Claims, 7 Drawing Sheets

(56) References Cited

U.S. PATENT DOCUMENTS

| | | | | |
|---|---|---|---|---|
| 7,047,846 B1* | 5/2006 | Hu | B25G 1/066 | 16/111.1 |
| 7,261,689 B2* | 8/2007 | Holland | A61B 17/00008 | 600/210 |
| 7,481,262 B2* | 1/2009 | Leeson | B63H 21/10 | 165/173 |
| 7,549,994 B2* | 6/2009 | Zander | A61B 17/1725 | 606/99 |
| 7,691,120 B2* | 4/2010 | Shluzas | A61B 17/3439 | 600/219 |
| 7,699,877 B2* | 4/2010 | Davison | A61B 17/0218 | 606/279 |
| 7,731,721 B2* | 6/2010 | Rathbun | A61B 17/1728 | 606/87 |
| 7,887,548 B2* | 2/2011 | Usher, Jr. | A61B 17/1735 | 606/104 |
| 7,938,832 B2* | 5/2011 | Culbert | A61B 17/1757 | 606/103 |
| 7,993,348 B2* | 8/2011 | Conte | A61B 17/1617 | 606/79 |
| 8,052,720 B2* | 11/2011 | Kuester | A61B 17/7037 | 606/246 |
| 8,152,720 B2* | 4/2012 | Loftus | A61B 17/7076 | 600/215 |
| 8,550,993 B2* | 10/2013 | Aferzon | A61B 1/32 | 600/210 |
| 8,690,879 B2* | 4/2014 | Kirschman | A61B 17/7032 | 606/86 A |
| 2005/0090822 A1* | 4/2005 | DiPoto | A61B 17/32002 | 606/86 A |
| 2005/0192486 A1* | 9/2005 | Hamel | A61B 1/32 | 600/226 |
| 2005/0245942 A1* | 11/2005 | DiPoto | A61B 17/3439 | 606/108 |
| 2006/0200186 A1* | 9/2006 | Marchek | A61B 17/0218 | 606/191 |
| 2007/0016223 A1* | 1/2007 | Pagliuca | A61B 17/0218 | 606/108 |
| 2007/0093828 A1* | 4/2007 | Abdou | A61B 17/025 | 606/86 A |
| 2007/0203399 A1* | 8/2007 | Gephart | A61B 1/32 | 600/219 |
| 2007/0233150 A1* | 10/2007 | Blain | A61B 17/17 | 606/96 |
| 2008/0132766 A1* | 6/2008 | Dant | A61B 17/02 | 600/219 |
| 2009/0036746 A1* | 2/2009 | Blackwell | A61B 17/02 | 600/219 |
| 2009/0149892 A1* | 6/2009 | Stad | A61B 17/7077 | 606/86 A |
| 2010/0198226 A1* | 8/2010 | Estes | A61B 17/025 | 606/90 |
| 2010/0217089 A1* | 8/2010 | Farley | A61B 17/02 | 600/213 |
| 2011/0245836 A1* | 10/2011 | Hamada | A61B 17/02 | 606/90 |
| 2011/0301422 A1* | 12/2011 | Woolley | A61B 17/0206 | 600/215 |

* cited by examiner

SCREW GUIDE AND TISSUE RETRACTOR INSTRUMENT

CROSS-REFERENCE TO RELATED APPLICATIONS

This application claims priority to provisional application Ser. No. 61/178,710 filed on May 15, 2009, which is incorporated herein in it's entirety by reference thereto.

FIELD OF THE INVENTION

The present invention relates to an instrument for guiding a screw and retracting soft tissue.

BACKGROUND OF THE INVENTION

During spinal surgery, there is a need to guide a screw into the spine and retract soft tissue around the surgery area. Previously, specific instruments are used to guide a screw into the spine and other specialized instruments are used to retract the soft tissue around the surgery area.

There is a need for a single instrument that allows the screw to be guided as well as retract soft tissue.

SUMMARY OF THE INVENTION

An apparatus for performing spinal surgery having a handle assembly, a screw guide, and a retractor. A shaft is provided with a handle, a neck portion and a connecting portion. The screw guide is provided with a connecting element coupled to the connecting portion of the handle assembly. A retractor for retracting tissue is coupled to the screw guide, wherein the neck portion of the handle assembly is provided with a spring loaded sleeve adapted to engage one of a plurality of holes positioned on a portion of the connecting element. The connecting portion is pivotably coupled to the connecting element.

BRIEF DESCRIPTION OF THE DRAWINGS

The invention will be more readily understood with reference to the embodiments thereof illustrated in the attached drawing figures, in which.

DETAILED DESCRIPTION OF THE INVENTION

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

Figures 1, 2:
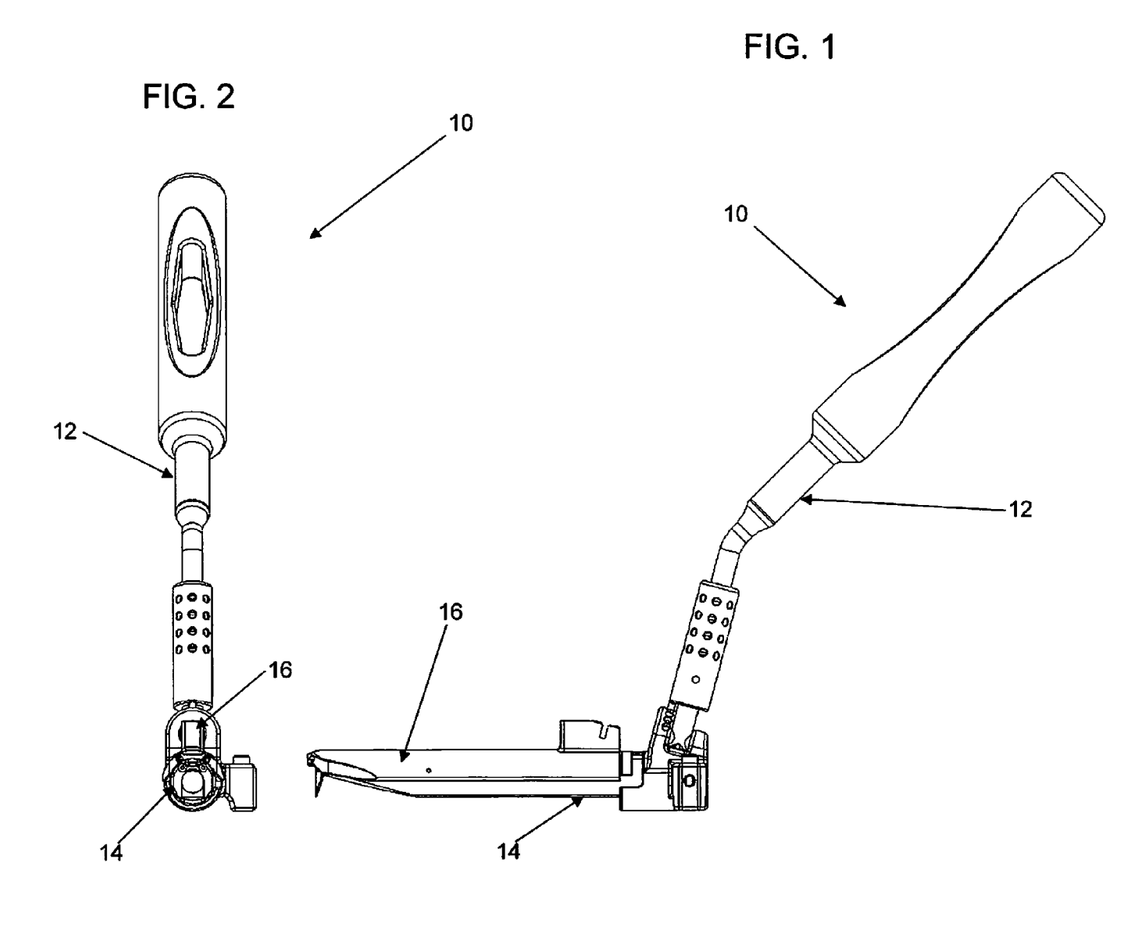
FIGS. 1 and 2 illustrate a front view and a side view of the drill guide and retractor system according to the present invention.

FIGS. 1 and 2 illustrate various views of the screw guide and soft tissue retractor system 10 according to one embodiment of the present invention. As illustrated in FIGS. 1 and 2, the system 10 is configured with a handle assembly 12, a screw guide 14, and a retractor 16. In one embodiment, the screw guide and soft tissue retractor system is utilized to stabilize the facets of the spine as an aid to fusion of adjacent vertebrae.

Figures 3, 4A:
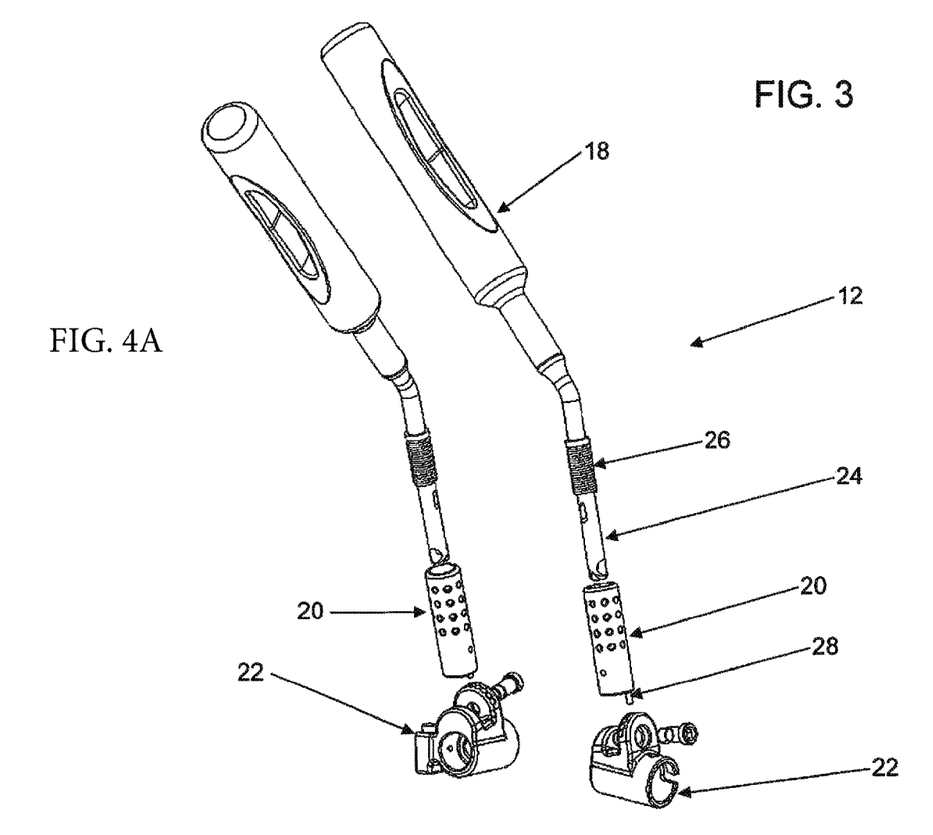
FIGS. 3 and 4A-4C illustrate exploded and perspective views of the handle assembly of the present invention.
Figure 4B:
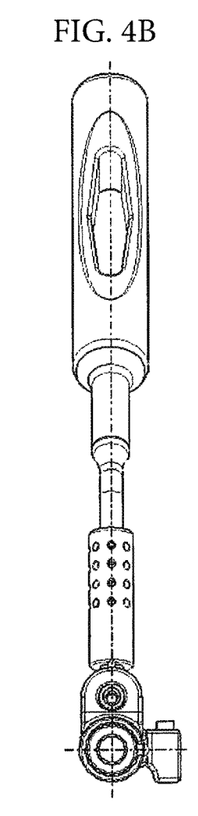
Figure 4C:
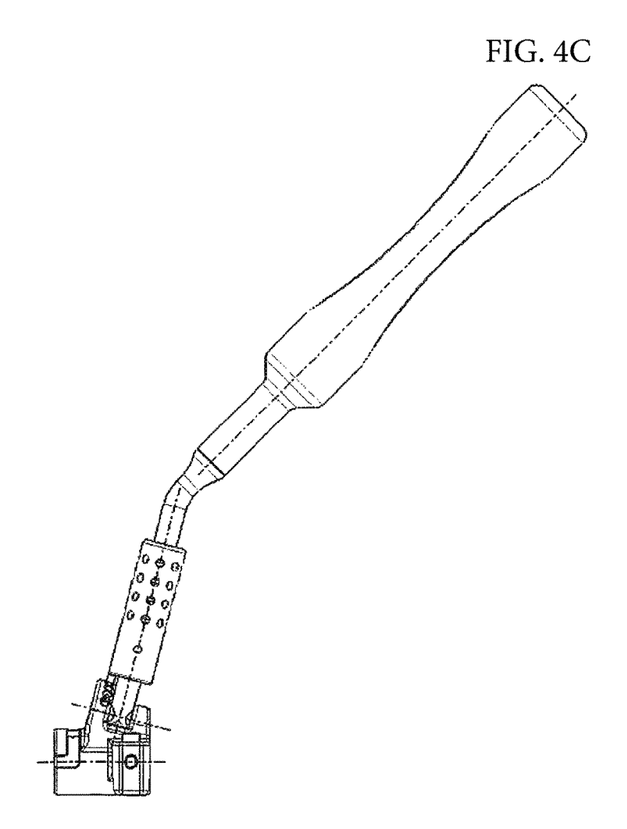

FIGS. 3 and 4 illustrate exploded views of the handle assembly 12 of the present invention. The handle assembly 12 is composed of a handle portion 18, a sleeve 20, and connecting element 22. The upper portion of the handle assembly is angled away from the blade and is designed not to interfere with the handle assembly of the drill guide. The handle angles away to avoid contact with soft tissue. The handle is also removable from the blade to eliminate interference when using other instrumentation.

Figure 5:
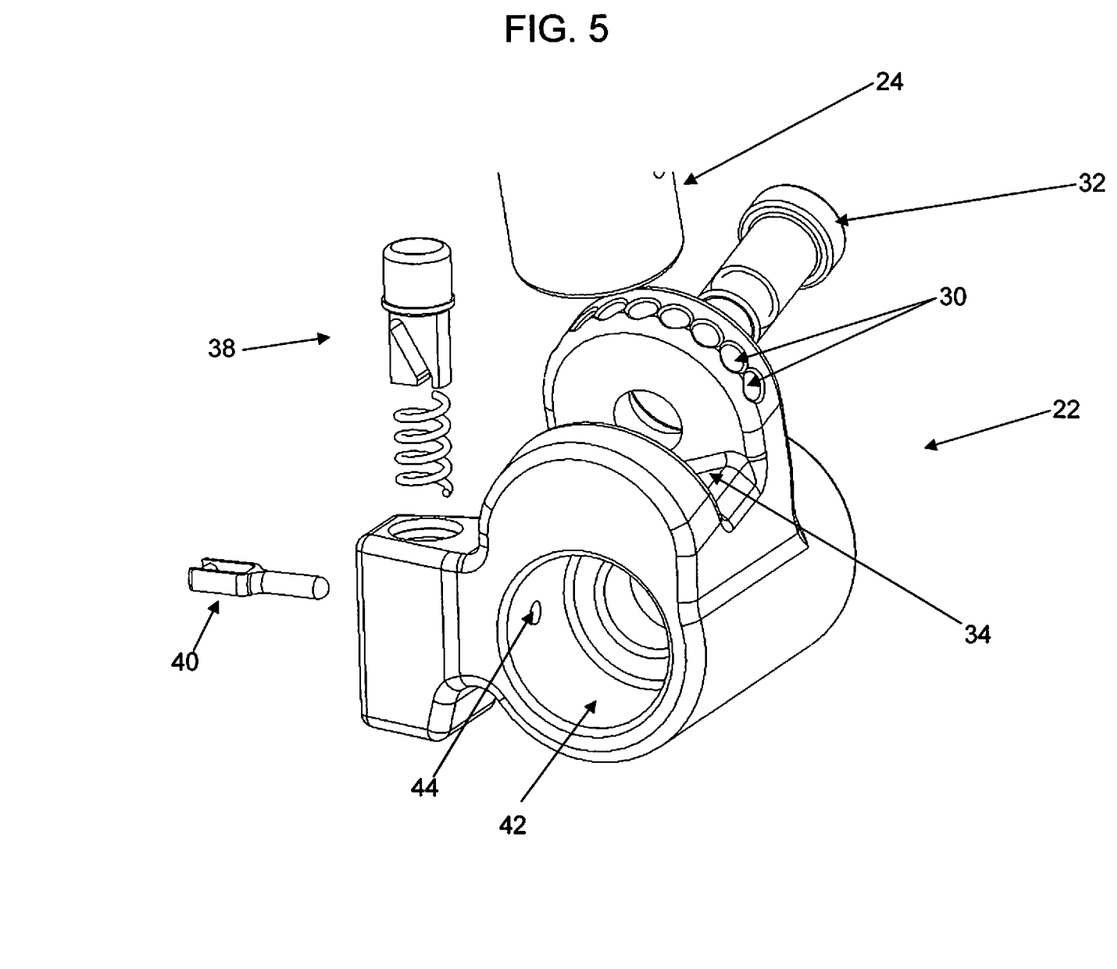
FIG. 5 illustrates an exploded view of the connection element of the handle assembly according to the present invention.

The sleeve 20 is adapted to enclose the shaft portion 24 of the handle assembly 12. FIGS. 3-5 illustrate the spring loaded sleeve 20 which works with the incremental cuts in a manner so that the spring loaded sleeve 20 is designed to be pulled back towards the handle to disengage the handle 12 from a standard orientation. The sleeve 20 will then snap into the next slot available automatically. This mechanism is a push button release and spring loaded lock which is used to secure the many proximal attachments that can be inserted into the handle assembly. The spring-loaded lock has a dowel 28 that enters one of the plurality of holes 30 which is designed to snap into a mating hole in the attachments. When adding an attachment, the part is automatically locked into the handle assembly. To remove the attachment, the user will push the button, which removes the dowel from the circular through way, thereby allowing the user to easily remove that attachment.

More specifically, the shaft portion 24 is provided with a spring 26 which the sleeve 20 encompasses when the system is assembled. The sleeve 20 is also provided with a dowel 28 and is designed to translate along the shaft portion 24, via the spring mechanism provided on the shaft portion 24 of the handle assembly 12. The dowel 28 is designed and configured to engage one of a plurality of holes 30 positioned on the connecting element 22. The handle assembly 12 is adapted to translate angularly within the connecting element 22. Once a position is selected for the handle assembly 18, the sleeve 20 is translated and the dowel 28 is fit into one of the plurality of holes 30. The connecting element 22 and handle assembly 12 may be coupled together through the use of pin 32 which extends through the hole 30 of the shaft portion 24 which secures the connecting element 22 to the handle assembly 12.

FIG. 5 illustrates an exploded view of the connecting element 22 according to the present invention. The connecting element 22 is configured to receive the shaft portion 24 of the handle assembly 12 in slot 34. As mentioned above, pin 32 is utilized to couple the shaft portion 24 to the connecting element 22. The shaft portion 24 once connected to the connecting element is pivotable so that the handle assembly 12 may be rotated into different predetermined locations. Also, on the connecting element 22, there is provided a mechanism for the screw guide 14 to be coupled to the connecting element 22, which is discussed in greater detail with regard to FIG. 6.

A spring loaded pin assembly 38 is utilized in another portion of the connecting element 22 to enable access to instruments other than the screw guide. For instance through hole 42 may be used to provide access to the surgical site for instruments such as a k-wire. Cannulas that enable this can be adapted to fit into the through hole 42. The spring loaded pin assembly 38 is configured to actuate pin 40. Pin 40 extends through the inner wall of the through hole 42 and extends out through hole 44. When the spring loaded pin assembly 38 is engaged, pin 40 is retreated from the through hole 36, thereby enabling a cannula or any other instrument to be positioned within the through hole 42. Once the instrument is positioned in the through hole, the spring loaded pin assembly 38 is disengaged, allowing pin 40 to engage the instrument and thereby locking the instrument within the connecting element 22.

Figure 6:
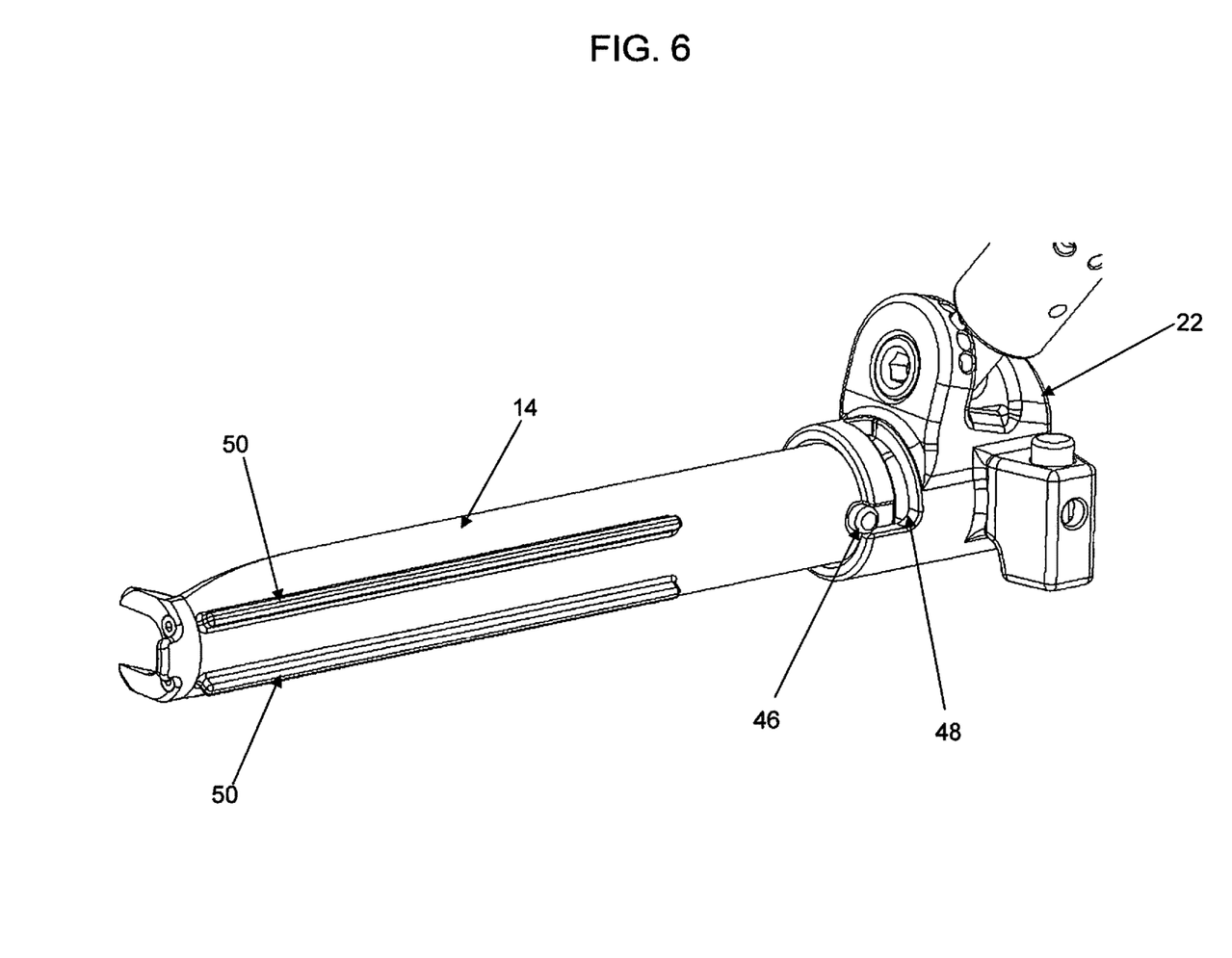
FIG. 6 illustrates the screw guide and the connection element according to the present invention.

FIG. 6 illustrates the screw guide 14 attached to the connecting element 22 of the present invention. The screw guide 14 is designed as a cannula that attaches to the connecting element 22. More specifically, the screw guide 14 is configured and dimensioned to be cylindrical in shape which enables a surgeon an easier access for insertion into soft tissue. The geometry of the screw guide 14 is also configured so that a continuous smooth surface is provided to eliminate the change of damaging the surrounding soft tissue. The screw guide 14 is further provided with protrusions on the bottom surface of the guide 14 to allow the guide to be docked or articulate on the fracture site. The distal end of the screw guide 14 has a bottom surface that matches the curve of the cervical spine in this particular embodiment of the invention. Although, the distal end may be configured to match the curve of any portion of the spine. The matching curvature of the distal end aides in establishing the trajectory of the instruments and implants.

Figures 7, 8:
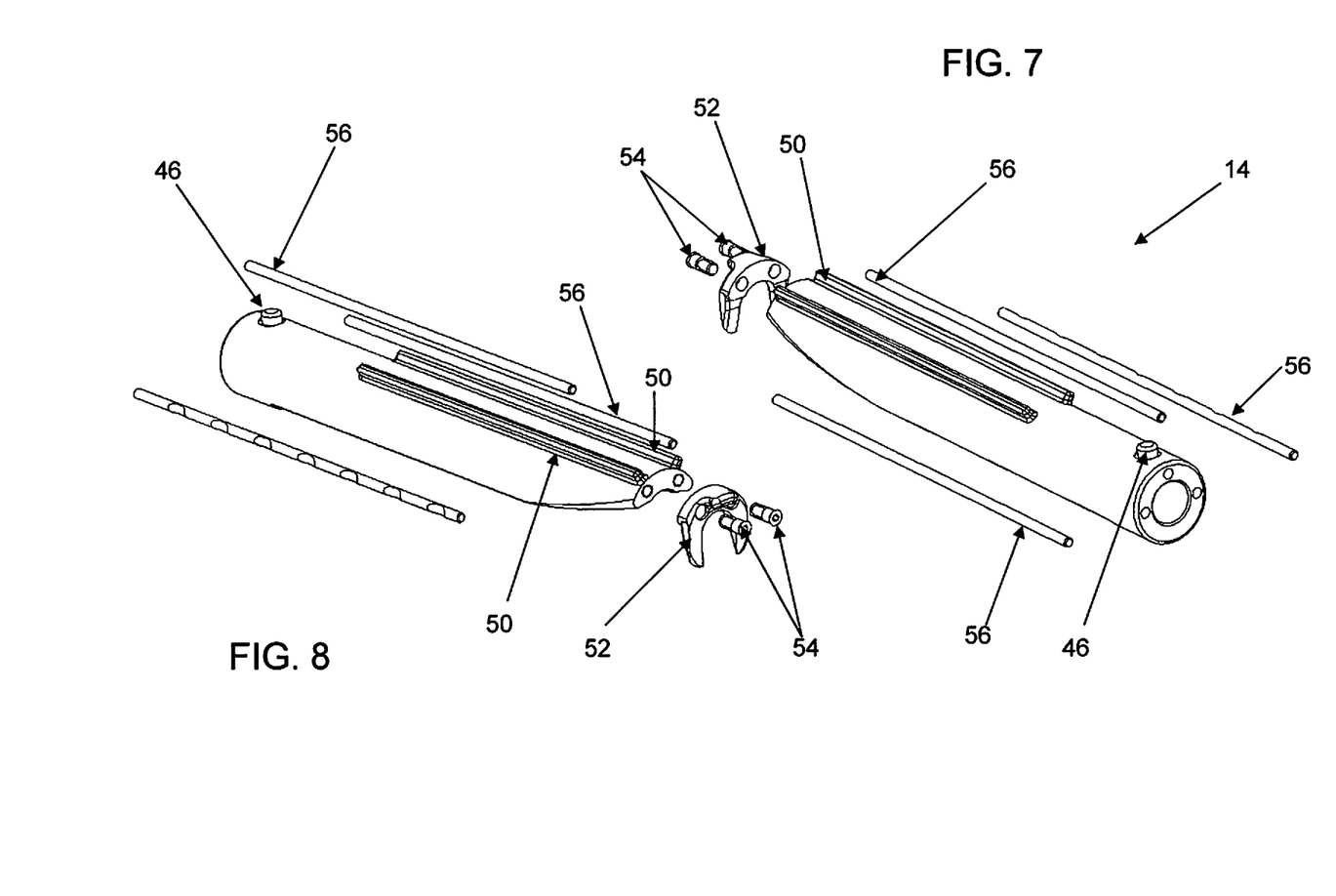
FIGS. 7 and 8 illustrate exploded views of the screw guide according to the present invention.

Now turning to FIGS. 7 and 8, the screw guide 14 will be discussed in greater detail. As illustrated in FIGS. 7 and 8, a connecting element 46 is provided on the top surface of the guide 14, and this connecting element 46 is the locking mechanism by which the screw guide 14 is attached to the handle assembly 12. The connecting element 46 is configured to fit into the slot 48 provided on the upper surface of the connecting element 22, as seen in FIG. 6. The screw guide 14 is also provided with rails 50 on the top surface that are spaced apart and angled to allow the screw guide to couple with the retractor. At the distal end of the guide, there is provided a protrusion 52 which is coupled to the distal end of the guide by pins 54, that is used to dock or articulate the screw guide 14 near or about the surgical site. The distal portion of the guide 14 also is configured to have a curvature which enables accessing the surgical site easier. The guide 14 is also configured with three radioopaque rods 56 with two rods being placed 180 degrees apart and one being positioned vertically, as illustrated in FIGS. 7 and 8. The rods 56 are used in conjunction with x-ray imaging to provide alignment verification through lateral and anterior-posterior x-ray images.

Figures 9, 10:
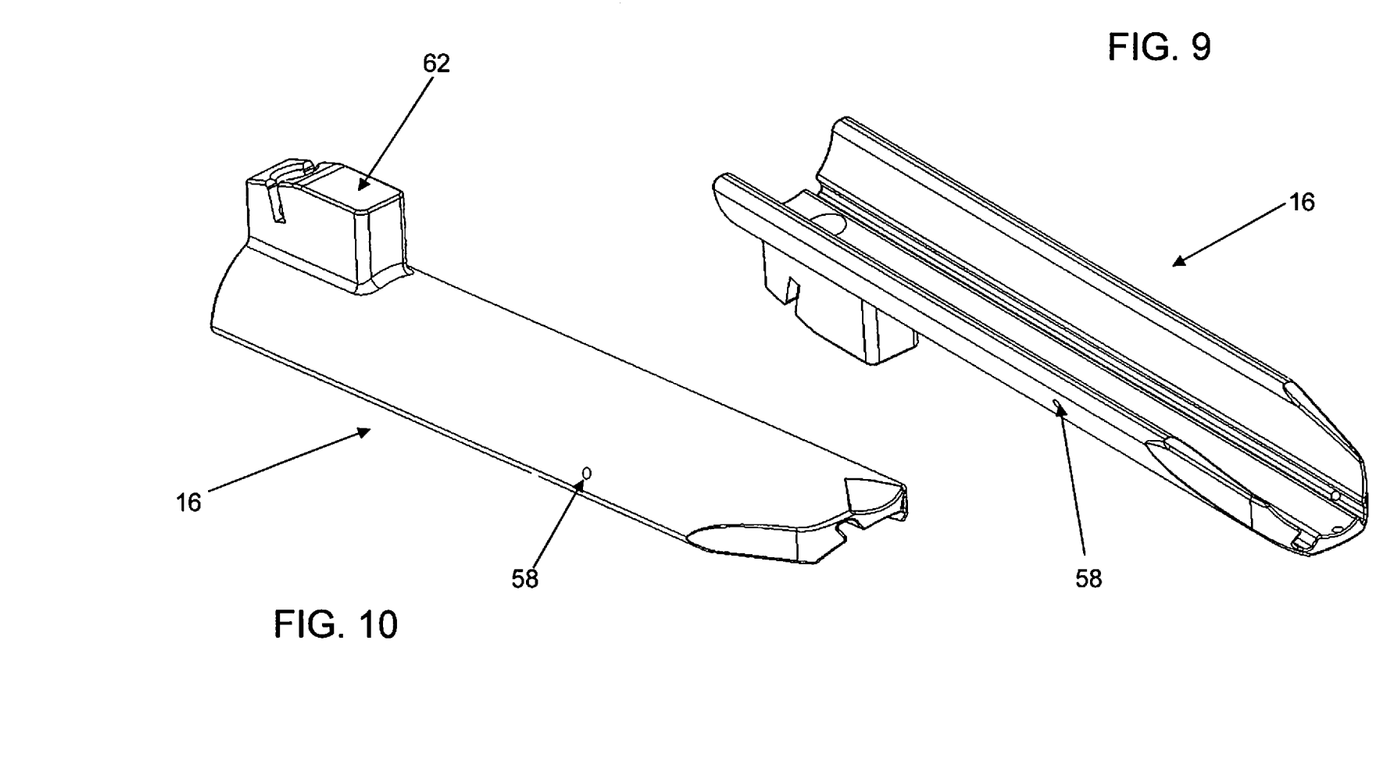
FIGS. 9 and 10 illustrate perspective views of the retractor according to the present invention.

FIGS. 9 and 10 illustrate the top and bottom views of the soft tissue retractor 16 in greater detail. The retractor 16 is utilized to access the surgical site and providing a safe cavity for inserting of the screw guide. The soft tissue retractor 16 is typically the first instrument assembled to the screw guide and the first instrument used. It is used for reaching the fracture side initially, and creates a safe cavity to the insert the screw guide. The tip of the soft tissue retractor 16 has a concave shape to match the anterior geometry of the normal cervical vertebral body. This allows the soft tissue retractor to be seated on the anterior body instead of having a flat tip that unstablizes the retractor.

The soft tissue retractor 16 also includes at least three radio opaque balls 58 that is pressed into the surface of the soft tissue retractor 16 that allows the user to verify the retractor's position through lateral and anterior-posterior imaging. At least two of the balls 58 will be visible when the retractor is level in the lateral plane while the ball at the tip will be visible when the retractor has reached the vertebral body. The retractor blade 16 is also composed of a radiolucent material so that the blade itself is visible in the x-ray images.

As further illustrated in FIG. 9, axial slots 60 are provided on the bottom portion of the retractor 16. These slots 60 are configured and designed to couple the retractor 16 with the rails of the screw guide. It should be noted that any mechanism for attaching the rails to the screw guide can be used. For example, a dove tail type connection can be used couple the screw guide to the retractor 16. FIG. 10 also illustrates the top portion of the retractor. In this particular embodiment, a connection assembly 62 is provided for attaching the retractor to another instrument such as a hex driver so that the surgeon may remove the retractor without removing the screw guide from the screw guide assembly.

While the invention herein disclosed has been described by means of specific embodiments and applications thereof, numerous modifications and variations can be made thereto by those skilled in the art without departing from the scope of the invention as set forth in the claims.

We claim:

1. An apparatus for performing spinal surgery comprising:
   a handle assembly comprising:
      a shaft having a handle, a neck portion and a connecting portion;
   a screw guide having a connecting element coupled to the connecting portion of the handle assembly; and
   a tissue retractor coupled to the screw guide,
   wherein the neck portion of the handle assembly comprises a spring loaded sleeve adapted to engage one of a plurality of holes positioned on a portion of the connecting element,
   wherein the connecting portion is pivotably coupled to the connecting element,
   wherein the screw guide includes a cylindrical body that forms an opening, wherein when the retractor is coupled with the screw guide the opening remains open,
   wherein the screw guide includes a protrusion on an outer surface of the cylindrical body and the connecting element includes an outer surface, an inner surface, and an elongated slot that extends from the outer surface to the inner surface and wherein the elongated slot receives the protrusion to attach the screw guide to the connecting element,
   wherein the handle is movably coupled to the connecting element such that the handle can pivot with respect to the connecting element and the screw guide.

2. The apparatus of claim 1, wherein the spring loaded sleeve comprises a dowel which is adapted to couple to one of the plurality of holes.

3. The apparatus of claim 1, wherein the retractor includes an arcuate body, wherein the cylindrical body of the screw guide is positioned in contact with the arcuate body of the retractor.

4. The apparatus of claim 3, wherein the screw guide is configured with a pin for engaging a screw guide receiving through hole.

5. The apparatus of claim 1, wherein the screw guide comprises first and second rails for engaging with the retractor.

6. The apparatus of claim 5, wherein the retractor is configured with at least two axial slots for engaging with the first and second rails of the screw guide.

7. The apparatus of claim 1, wherein the retractor comprises an instrument engaging element positioned on an outer surface of the retractor.

8. The apparatus of claim 1, wherein the retractor and the screw guide comprise radioopaque markers.

9. The apparatus of claim 1, wherein the screw guide comprises a distal end having protrusions to access a surgical site.

10. An apparatus for performing spinal surgery comprising:
   a handle assembly comprising:
      a shaft having a handle, a neck portion and a connecting portion;
   a screw guide having a connecting element coupled to the connecting portion of the handle assembly; and
   a tissue retractor coupled to the screw guide, wherein the connecting portion is coupled to the connecting element,
   wherein the screw guide includes a cylindrical body that forms an opening, wherein when the retractor is coupled to the screw guide the opening remains open,
   wherein the screw guide includes a protrusion on an outer surface of the cylindrical body and the connecting element includes an outer surface, an inner surface, and an elongated slot that extends from the outer surface to the inner surface and wherein the elongated slot receives the protrusion to attach the screw guide to the connecting element, and
   wherein the handle is movably coupled to the connecting element such that the handle can pivot with respect to the connecting element and the screw guide.

11. The apparatus of claim 10, wherein the neck portion of the handle assembly comprises a spring loaded sleeve adapted to engage one of a plurality of holes positioned on a portion of the connecting element.

12. The apparatus of claim 11, wherein the spring loaded sleeve comprises a dowel which is adapted to couple to the one of a plurality of holes.

13. The apparatus of claim 10, wherein the retractor includes an arcuate body, wherein the cylindrical body of the screw guide is positioned in contact with the arcuate body of the retractor.

14. The apparatus of claim 13, wherein the screw guide is configured with a pin for engaging a screw guide receiving through hole.

15. The apparatus of claim 10, wherein the screw guide comprises first and second rails for engaging with the retractor.

16. The apparatus of claim 15, wherein the retractor is configured with at least two axial slots for engaging with the first and second rails of the screw guide.

17. The apparatus of claim 10, wherein the retractor comprises an instrument engaging element positioned on an outer surface of the retractor.

18. The apparatus of claim 10, wherein the retractor and the screw guide comprise radioopaque markers.

19. The apparatus of claim 10, wherein the screw guide comprises a distal end having protrusions to access a surgical site.

20. A method for accessing a surgical site for spine surgery comprising the steps of:
   determining an angle for approaching the surgical site;
   connecting a shaft having a handle portion to a connecting element through manipulation of a sleeve at the determined angle for approaching the surgical site;
   connecting a screw guide to the connecting element, wherein the screw guide includes a protrusion on an outer surface and the connecting element includes an outer surface, an inner surface, and an elongated slot that extends from the outer surface to the inner surface and wherein the elongated slot receives the protrusion to attach the screw guide to the connecting element;
   connecting a retractor to the screw guide;
   placing the guide on the surgical site;
   using the retractor to retract tissue away from the surgical site; and
   inserting a screw into bone elements at the surgical site,
   wherein the screw guide includes a cylindrical body that forms an opening, wherein when the retractor is coupled to the screw guide the opening remains exposed, and
   wherein the handle portion is movably coupled to the connecting element such that the handle can pivot with respect to the connecting element and the screw guide.

* * * * *